United States Patent [19]
Scott

[11] 3,979,522
[45] Sept. 7, 1976

[54] BIOCHEMICAL PROCESS FOR THE SYNTHESIS OF PROTEIN FROM CELLULOSE AND STARCH-CONTAINING PLANTS

[76] Inventor: Henry L. Scott, 204 E. Houghton, Tuscola, Ill. 61953

[22] Filed: Aug. 13, 1975

[21] Appl. No.: 604,239

[52] U.S. Cl. .................................. 426/18; 426/52; 195/31 R; 195/82
[51] Int. Cl.² .......................................... A21D 2/00
[58] Field of Search .................. 195/31, 4, 7, 8, 11, 195/82; 426/18, 52

[56] References Cited
UNITED STATES PATENTS 3,637,396   1/1971   Hollo et al. ........................... 195/82

OTHER PUBLICATIONS

Brook et al., "Fermentation Methods for Protein Enrichment of Cassava" Cited in Chemical Abstracts vol. 72:65518f.

Primary Examiner—A. Louis Monacell
Assistant Examiner—R. B. Penland
Attorney, Agent, or Firm—Burmeister, York, Palmatier, Hamby & Jones

[57] ABSTRACT

A biochemical process for the synthesis of protein from cellulose and starch-containing plants, such as tubers, aroids and dioscorea, and particularly from cassava comprising grinding the plant to a meal, making an aqueous slurry with the meal, heating the slurry under steam pressure and releasing the pressure to remove prussic acid as a vapor from prussic acid-containing plants such as cassava, then enzymatically hydrolyzing the starch of the plants to sugars, introducing into the mixture a food yeast, for example, *Candida utilis* var. *major* and growing the yeast at a temperature of 60°–70°F for at least 4 hours at a pH of 4.0–6.5 while introducing ammonia and air during the growth of the yeast, and then evaporate water from the slurry thereby obtaining a solid of 45–70 per cent protein suitable for use as a food supplement.

11 Claims, No Drawings

BIOCHEMICAL PROCESS FOR THE SYNTHESIS OF PROTEIN FROM CELLULOSE AND STARCH-CONTAINING PLANTS

BACKGROUND OF THE INVENTION

The invention relates to a biochemical process for the synthesis of protein from cellulose and starch-containing plants, including such plants as tubers, aroids and dioscorea, as for example, tubers such as cassava and other plants of the genus Manihot; aroids, such as taro; and dioscorea, such as yams.

The invention is especially concerned with a biochemical process for making a high protein food supplement from cassava, sometimes also called manioc, yuca or Manioca, and scientifically called *Manihot escuelenta*. The term "cassava" is used in this specification and claims to identify this material.

Cassava includes both the bitter and sweet cassava, both containing prussic acid, the bitter cassava having a higher amount of prussic acid.

I have discovered that the prussic acid must be substantially all removed in order to obtain satisfactory yields by the biochemical process disclosed herein.

Cassava is deficient in protein, a fact that is generally true for tubers, aroids and dioscorea. Tubers from various sources analyzed 1.5 to 3.0 per cent by dry weight of protein. Plants that store large amounts of starch and moisture, as do these plants, invariably are deficient in protein. These plants, however, can be grown on a large scale on land not presently used for crops.

My process of synthesizing protein from such starchy plants is therefore of great importance. It gives the world a process which can be used with a major food crop capable of giving a high yield and producing a higher percentage of starch that can be converted to sugars on which to grow yeast that synthesizes single cell protein of high amino acid content suitable for use as a food supplement.

SUMMARY OF THE INVENTION

In accordance with this invention a cellulose and starch-containing plant is treated to hydrolyze the starch to sugars preferably by means of a hydrolyzing agent such as a hydrolyzing enzyme, then a food yeast is added to the mixture and the yeast is grown aerobically on the sugars present in the mixture while introducing ammonia into the composition during growth of the yeast for a time sufficient to produce a substantial amount of protein in addition to the protein originally present in the plant. Air is introduced in addition to the ammonia during the yeast growth to insure aerobic fermentation and to avoid anaerobic fermentation which produces alcohol.

In one embodiment of the invention the cassava or other starch-containing plant of the type of tubers, aroids and dioscorea is ground to a meal, the meal dried to a moisture content of, for example, 6–10 per cent, an aqueous slurry made with the meal of, for example, 4–15 per cent solids, preferably not higher than this, the slurry heated under steam pressure of preferably 20–125 psi, hydrolyzing the starches of the composition enzymatically to sugars, adding a food yeast to the mixture, growing the yeast aerobically on the sugars, feeding the yeast in the composition with anhydrous ammonia during growth and drying the composition by evaporation to a final moisture content of, for example, 10–12 per cent by weight.

A very important part of the process is the removal of the prussic acid and any $CN^-$ radical from the composition prior to yeast growth. Maximum production of yeast is not accomplished unless the $CN^-$ radical is completely eliminated. A preferred way of doing this is to release the steam pressure during heating of the slurry. The release of the steam carries with it the prussic acid in the plants.

Any food yeast may be used in the process. Highly satisfactory results have been attained with *Candida utilis*, var. major, including mutants thereof, *Saccharomyces carlsbergensis* and *Saccharomyces cerevisiae*.

*Candida utilis* var. major, is the preferred strain of yeast because it is a large cell yeast which proliferates very rapidly under aerobic conditions and utilizes ammonia efficiently to synthesize all of the essential amino acids. It utilizes more different monosaccharides and disaccharides than any other species or variety of yeasts, which means higher yields of yeast per pound of starch. It is the highest of the three acceptable yeasts in production of protein, producing up to 68 per cent protein. It is also the highest producer of the water soluble vitamines of the three yeasts, but the other two produced adequate amounts. Protein from yeasts, bacteria and algae has become known as Single Cell protein. (See Table I for analyses of the three yeasts.)

TABLE I

GROSS COMPARISON OF FOOD YEASTS

|  | C. Utilis Food | S. Carlsbergensis Brewers | S. Cereviviae Distillers |
| --- | --- | --- | --- |
| Moisture | 5.8% | 4.7% | 7.0% |
| Nitrogen(× 6.25 for protein) | 8.0% | 7.9% | 6.6% |
| Purine N | 0.4% | 0.4% | 0.4% |
| Polysaccharide | 29.6% | 30.7% | 34.0% |
| Fat | 4.8% | 2.6% | 7.5% |
| Fiber | 0.8% | 0.4% | 1.5% |
| Ash | 9.7% | 7.3% | 6.1% |
| Thiamin | 50.0 ug | 136.0 ug | 65.0 ug |
| Riboflavin | 45.0 ug | 38.0 ug | 52.0 ug |
| Niacin | 415.0 ug | 525.0 ug | 195.0 ug |
| Pyridoxine | 29.0 ug | 40.0 ug | 26.0 ug |
| Pantothenic acid as calcium pantothenate | 35.0 ug | 25.0 ug | 15.0 ug |
| Biotin | .80 ug | .80 ug | .8 ug |
| Folic acid | 4.0 ug | 6.0 ug | 5.0 ug |
| Choline (as choline chloride) | 5,800 IU | 4,000 IU | 3,500 IU |

NOTE: All vitamin figures except choline are in micrograms per gram. All figures thru "ash" are in per cent of solids. Choline chloride is reported in international units (IU)

The true yam as well as cassava may be used as a raw material, but yields probably could not be made to approach cassava, and the yam is much more exacting in its soil characteristics and rainfall demands. It is also subject to rotting under damp conditions. The giant yam, *Dioscorea escuelenta*, has possibilities. Under conditions of good rainfall and ideal fertilization, high yields have been reported. Another dioscorea, *Pachyrrhizus erosus*, a native of Mexico and Central America, has now been naturalized in various tropical soils. It prefers sandy loams like cassava, and yields up to 95 tons per hectare have been reported. It reproduces from seeds and attains maturity in about 8 months.

Aroids such as taro are grown and eaten by people, but would only be of interest if it were necessary to use waterlogged or swampy soil. Yields are not high.

Tubers, aroids and yams are eaten throughout the world for their starch, but in general, they range in protein from 2–3 per cent. All of the tubers are high in moisture when first harvested.

Fresh cassava may contain over 50 per cent moisture, so that yields per acre in pounds are really somewhat deceptive. However, for the purpose of this invention, the total weight of starch produced is most important. Cassava may contain up to 70 per cent starch but it varies widely according to the type of soil, texture of soil, and rainfall.

The still damp meal goes from the press into a tunnel drier on a continuous conveyor where it is dried to 10–12 per cent moisture. The length of the tunnel is determined by the amount of moisture left after squeezing, the thickness of the bed of meal, and the final degree of moisture desired. The dried meal may then be shunted to storage bins or sent directly to the plant for further processing.

There are three ways of processing cassava for the biochemical synthesis of protein. They are the discontinuous feeding batch process, the continuous process, and the true batch process.

Discontinuous feeding is simply adding media containing sugar to the fermenter as the yeast uses up the sugar. The reason for this method is that above 10 per cent concentrations of sugar inhibit the multiplication of yeast. This method requires no extra equipment if the plant is designed for batch processing.

Continuous processing is the ultimate in automation. It is truly the push button plant. Each step of the process is specially designed and the media is pushed along by steam-air pressure or conveyor. Steam pressure is controlled by sensor gauges and solenoid valves, pH is automatically controlled by probes, each step is timed precisely, and product is taken off at the same rate that media is fed in. Continuous processing is very inexpensive to operate, once the system is in balance, and there

TABLE II

ANALYSIS OF CASSAVA, YAMS AND AROIDS

| Species | % Solids | % Starch | % Protein | % Phosphorus | % Potassium | Dry Basis % Magnesium | % Manganese |
|---|---|---|---|---|---|---|---|
| Cassava Manihot | 45–55 | 55–70 | 1.47–3.08 | | | | |
| Escuelenta with bark | | | | 0.55 | 0.50 | 0.50 | 0.30 |
| without bark | | | | 0.31 | 0.38 | 0.39 | 0.29 |
| Yam Dioscorea Alata | 55 | 45–50 | 7.0 | 1.00 | 0.70 | 0.60 | 0.50 |
| Aroids Colocasia Escuelena | 42–45 | 40–50 | 5.0 | 0.66 | 0.50 | 0.60 | 0.50 |

This analysis includes the elements and compounds essential to the maximum growth of yeast. All of the tubers, aroids, and yams are usually deficient in phosphorus, potassium, magnesium and manganese. This is to be expected in tropical soil, and these nutrient elements may be added to the fermenter yeasts. Yeasts are also known to require biotin, but the requirements are small and can also be added to the fermenters.

Solids vary with the amount of rainfall and the age of the tubers when analyzed. Starches and proteins vary with the climate and type of soil.

In processing for protein synthesis, the entire plant is put through a mill and ground to a coarse meal — coarse enough to prevent dusting, yet fine enough to make the starch readily available. A Wiley mill has been used in the laboratory with great success in grinding the wet meal to pass through a 20 or 30 screen.

The damp meal goes continuously through a two-roll press to squeeze out the water. This squeezing removes part of the water and about half of the prussic acid. The juice tested about 71 PPM prussic acid plus about 6 per cent protein, based on a solids content of 10 per cent. Cassava holds moisture tenaciously. Some cassava under 12,000 lbs. pressure was squeezed until it formed a solid cake. It still contained 30–35 per cent moisture.

is unusual uniformity of product. Spray drying is almost a must.

DESCRIPTION OF PREFERRED EMBODIMENT

The batch process will be described in detail because the continuous process simply applies modern technology to the fundamental method. A slurry is prepared by mixing 1 part by weight of cassava with 3–5 parts by weight of water in a large pressure cooker equipped with rake-type agitation. It is cooked at pressures ranging from 20 to 125 pounds of steam per square inch for 20 to 30 minutes, depending on the amount of prussic acid (HCN) in the meal and also upon the amount of starch present. The amount of water may also vary with the starch content, because very high amounts of starch tend to gel, and that means dismantling the entire system and cleaning it.

This pressure cooking is an important step, because it not only makes the starch available by breaking down the walls of the starch cells, but it completely eliminates the prussic acid. Repeated tests have failed to show any HCN residues. HCN is bound to the glucosides in the cassava and the heat and sudden release of pressure causes the HCN to volatilize. This is usually accomplished by fermenting, boiling or cooking after maceration, but I have found that these methods always yield measurable residues of HCN.

The elimination of prussic acid is doubly important, because it has been found impossible to get a yeast count above $6 \times 10^6$ per ml. with 71 Ppm HCN present. The CN radical blocks the Krebs cycle and interferes with the respiration of the yeast. Maximum production of yeast is not accomplished unless CN is completely eliminated.

After the slurry is pressure cooked, it is pumped to one of two converters where it is cooled to 148°–150° fahrenheit. The converters are equipped with rake-type agitators. Two converters are used to permit uninterrupted operation.

While the temperature of the converter is maintained between 148°–150°F, a solution containing equal parts of pure A and B amylase is added in amounts depending on the amount of starch present and upon the dilution of the amylases.

As an alternate to the use of the concentrated enzymes, there may be used up to 10 per cent of barley malt, which was ground to pass a 30–60 mesh screen. Barley malt converts the starch into sugars within a half-hour, with efficiencies up to 100 per cent. Monosaccharides and disaccharides are produced, with glucose predominating by a wide margin. This is why *Candida utilis*, var. major, is preferred because it can utilize a greater number of disaccharides, thus squeezing a little more efficiency out of the fermentation process.

After converting the starch to sugars, the slurry is pumped to giant fermenters through heat interchangers. The temperature is brought down to 60°–70°F, at which time the pH of the slurry is carefully adjusted to 4.0 to 6.5, preferably 4.0. Lactic acid is preferred but larger amounts of other organic acids may be used if not too expensive.

The yeast is prepared and grown separately. Preparation may be either batch or continuous, and may be grown either in a closed system or in open tubs. Yeast should first be grown in the laboratory in 200 ml flasks containing corn mash. After growing for several generations one should start adding increasingly larger amounts of cassava meal until the yeast is growing on a slurry of pure cassava. This gradual adaption of the yeast is necessary, because in all probability, no domestic yeast has ever been grown on cassava. The yeast is then grown in a 3-liter flask which is used to inoculate the plant yeast. A separate system is established by making a slurry, cooking under pressure, acidifying, converting and cooling. The laboratory yeast is then inoculated and grows until the cell count is at least $5 \times 10^8$, or preferably $6 \times 10^9$. It is then pumped to the fermenter. Initial cell mass should not be less than 2 per cent by volume of the contents of the fermenter, but a total mass of 10 per cent will grow up faster.

It is necessary to inject a note of warning at this point. Cassava is not only deficient in protein but is usually deficient, from the point of view of maximum yeast growth and food value, in phosphorus and some of the trace minerals, such as cobalt, copper, potassium, manganese and magnesium. Yeast specifically requires phosphorus and many of these trace minerals for maximum growth. Yeast also requires biotin for maximum growth, but this need not be added since it is present in food yeasts in adequate amount.

These mineral deficiencies preferably should be determined for each batch of cassava, preferably with an atomic adsorption spectrophotometer, and added in minor amounts to both the yeast media used as inoculum and to the media in the fermenter to obtain maximum growth. For example, at least 1 per cent of phosphorus and a few parts per million of the other elements, based on the dry ash, will speed up growth.

If these trace minerals and biotin are added during the process, they will not have to be added to the finished product.

By using a large inoculum and growing the yeast aerobically instead of anaerobically, a maximum cell mass is produced and water, acid, and $CO_2$ are produced instead of alcohol. Using Candida utilis and this method, yields of up to 70 per cent protein have been achieved.

Peak yields of cells may be attained in from 4 to 12 hours. The time to "drop a fermenter" can be determined by testing for dead cells or determining the residual sugar by saccharimeter. The test is a simple staining technique using methylene blue. If more than 10 per cent of the cells are dead, they have used up all of their food.

The fermenters deserve special discussion, because getting maximum aeration in large amounts of liquid presents a special problem. The fermenters used are copper-steel or stainless steel tanks, with the tops enclosed and possessing a clean-out hatch that can be opened and closed. Inside is a double or quadruple series of grids, composed of pipe, attached to the wall of the fermenter at different levels. The circular spargers are attached to crossover pipes of the same size and each pipe has a hole drilled on the upper side at a distance of 3 feet. The size of the holes will be determined by the depth of the slurry and its total volume. These will form a kind of a grid that permits air to be injected equally, so that the fermenter will be aerated equally throughout. Paralleling each tube and attached to the pipes are other pipes approximately one-half the diameter of the aeration pipes, which are of extreme importance, because these are for injecting anhydrous ammonia. Yeast of any species, will take up ammonia and use it to synthesize all of the amino acids, without utilizing any of the protein in the cassava. This is important, because cassava has only 1–3 per cent protein and the yeast would grow poorly. I have preferred to use anhydrous ammonia, $NH_3$, instead of ammonium hydroxide, $NH_4OH$, because that would introduce additional water. Ammonia addition should be controlled by a continuous controlling and recording pH meter.

When cell counts reach maximum, the fermenter is "dropped" to a well to permit washing out and sterilizing the fermenter with steam to prevent contamination. Maximum cell counts are usually $6 \times 10^{10}$ per ml. Continuous operation is accomplished with this method.

In one method, the contents of the well are pumped into either a five-step or seven-step series of evaporators which are heated by steam. A vacuum is pulled, either with a steam jet or high pressure water jet. The evaporation is by thin film which comes in contact with counter current steam. It takes roughly a pound of steam to remove a pound of water. The slurry is evaporated down to a thick syrup which will not solidify as long as it is kept hot. The syrup is 15 to 20 per cent water.

The syrup is pumped over dehydrators, which are steam heated drums rotating inward on each other that pick up a thin film of the syrup. A knife edge on the front end of the drum cuts the film off and it drops into a screw conveyor which chops it into flakes of assorted sizes. It comes off of the rolls just like a sheet of paper. The final product is 8–12 per cent moisture. See Table III for analysis of the final product, which includes the cellulosic contents of the cassava, the original 3 per cent protein plus what minerals were present and have been added.

There has been obtained by the process of this invention in actual practice from 45 to 70 per cent protein with excellent amino-acid distribution. See Table IV. Forty-five per cent protein is equivalent to or exceeds soya protein and 70 per cent protein exceeds most fish meal.

Also there is obtained very high vitamin content with the exception of the vitamins A, D and E. *Candida utilis* produces 4–5 per cent fats which yield a fair amount of these vitamins.

fine flour, mixing the flour with water, cooking under at least 20 lbs. of pressure and drying down to 6–10 per cent moisture. Final drying may be accomplished by a tunnel drier or drum drier, followed by grinding to pass a 200 mesh screen. This makes excellent flour which can be blended with the high protein supplement to produce a completely balanced food. The flour makes excellent bread, can be made into pancakes, etc., and be flavored with any of the recently developed essences.

The high protein supplement may be used immediately in this country as cattle feed, hog feed, chicken feed and cat and dog food. This would take the pressure off of corn and soya meal for cattle feeders, thus permitting greater amounts for export.

This product may also be formulated for human food,

TABLE III

ANALYSIS OF HIGH PROTEIN YEAST SINGLE CELL SUPPLEMENT

| Tests | Range | Average | Explanation |
|---|---|---|---|
| % Moisture | 8–13 | 11 | Tunnel dried |
| % Starch | 18–22 | 20 | Mostly synthesized by yeast |
| % Total Protein | 50–70 | 60 | Yeast fed anhydrous $NH_3$ |
| % Crude Fiber | 1.5–2.5 | 2.0 | Include bark of roots |
| % Crude Fats | 2.0–4.0 | 3.0 | About 0.2% in cassava |
| % Ash | 2.0–4.0 | 4.0 | Contains minerals |
|   |   | 100.0% |   |
| % Trace and other minerals in Ash |   |   |   |
| Calcium - |   | 2.0 | These trace minerals are required for maximum |
| Phosphorus - |   | 1.8 | growth of yeast or were already in the cassava. |
| Sodium - |   | .02 | They are not dictated by nutritional require- |
| Potassium - |   | .033 | ments of animals and man. Where animal and human |
| Magnesium - |   | .020 | requirements exceed that of yeast, they can be |
| Manganese - |   | .030 | added to the finished product by a propor- |
| Copper - |   | .010 | tionator at the conveyor. |
| Cobalt |   | Tr. |   |
|   |   | 3.913% |   |

Vitamins - See Table I
Vitamins - A, D and E not included.

TABLE IV

*AMINO ACID DISTRIBUTION IN SINGLE CELL PROTEIN SUPPLEMENT, CANDIDA UTILIS VAR. MAJOR AND MUSCLE PROTEIN
(In percent of total protein)

| Amino Acids | ⊕Single Cell Protein Supplement Food Supplement | Candida utilis yeast var. major Food Yeast | Muscle Protein (beef) |
|---|---|---|---|
| Argenine | 5.2 | 4.1 | 7.1 |
| Histidine | 2.8 | 1.0 | 2.1 |
| Lysine | 8.1 | 4.5 | 7.9 |
| Tyrosine | 5.0 | 4.2 | 3.0 |
| Tryptophane | 1.4 | 1.2 | 1.1 |
| Cystine | 1.4 | 1.0 | 1.3 |
| Methionine | 3.0 | 0.83 | 3.4 |
| Threonine | 5.5 | 5.42 | 3.3 |
| Leucine | 13.6 | 7.52 | 12.2 |
| Isoleucine | 3.9 | 4.2 | 3.2 |
| Valine | 6.0 | 6.08 | 7.0 |
| +Percent Total Protein | 50–70% | 55% | 40% |

*Done on the amino acid analyzer
+Done on Kjeldahl apparatus
⊕Fed anhydrous ammonia
NOTE: This table shows that Single Cell Protein Supplement Protein is quite comparable to Muscle Protein. The feeding of ammonia improves the distribution of amino acids and there are no deficiencies.

There may also be produced cassava flour which is completely free from traces of HCN. The process involves peeling the tubers, automatically, grinding to a fine flour, mixing the flour with water, cooking under at especially in the developing countries. The supplement may be mixed with its own starch, and prepared as a balanced flour, or into any of the prepared food products of today. The product may be processed into cereals in the customary ways.

I claim:

1. A biochemical process for the synthesis of protein from cellulose and starch-containing plants, said plants including a compound containing a $CN^-$ radical, which comprises hydrolyzing the starch therein to sugars, substantially removing said $CN^-$ compound, introducing a food yeast to the mixture and aerobically growing the food yeast on the sugars while introducing ammonia into the mixture during growth of the yeast, said $CN^-$ compound being removed prior to growing the yeast.

2. The process in accordance with claim 1 in which the plant contains prussic acid and the prussic acid is substantially removed prior to growing the yeast.

3. The process in accordance with claim 2 in which the plant is cassava.

4. The process in accordance with claim 1 in which the plant is cassava.

5. The process in accordance with claim 4 in which the added yeast is first prepared and grown separately in corn mash, and then cassava meal added to the corn mash in increasingly larger amounts until the yeast is growing on a slurry of substantially pure cassava.

6. The process in accordance with claim 1 in which the plant in the form of a ground meal is an aqueous slurry and the starch is enzymatically converted to sugars.

7. The process in accordance with claim 6 in which the slurry is heated under steam pressure of 20–125 psi and the prussic acid is removed from the composition by releasing the pressure.

8. The process in accordance with claim 1 in which phosphorus in at least 1 per cent of the dry ash is present in the mixture.

9. The process in accordance with claim 1 in which the yeast is *Candida utilis* var. major.

10. A biochemical process for the synthesis of single cell protein, suitable for use as a food supplement, from cassava containing prussic acid which comprises grinding the cassava plant to a meal, drying the meal to a moisture content of 6–11 per cent by weight, making an aqueous slurry with the meal of not higher than 10 per cent solids, heating the slurry under steam pressure of 20–125 psi to remove prussic acid, enzymatically hydrolyzing the starches of the composition to sugars, introducing *Candida utilis* var. major into the mixture, growing the yeast at approximately 70°F with the pH of the slurry adjusted to 4.0 for at least 4 hours while introducing ammonia and air into the mixture, thereby producing single cell protein, evaporating the slurry to a moisture content of 8–12 per cent thereby obtaining a solid of 45 to 70 per cent protein.

11. The process in accordance with claim 1 in which the plants are tubers, aroids or dioscorea, and the $CN^-$ compound is a volatile compound removed from the mixture by heating an aqueous slurry of the mixture under substantial steam pressure.

* * * * *